US011344704B2

(12) United States Patent
Spataro et al.

(10) Patent No.: US 11,344,704 B2
(45) Date of Patent: May 31, 2022

(54) CATHETER SYSTEM FACILITATING REDUCED DRAG FORCE

(71) Applicant: Becton, Dickinson and Company, Franklin Lakes, NJ (US)

(72) Inventors: Joseph Spataro, Cottonwood Heights, UT (US); S. Ray Isaacson, Layton, UT (US); Zhee Min Jimmy Yong, Telok Kurau (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 28 days.

(21) Appl. No.: 16/921,494

(22) Filed: Jul. 6, 2020

(65) Prior Publication Data

US 2021/0008350 A1  Jan. 14, 2021

Related U.S. Application Data

(60) Provisional application No. 62/873,088, filed on Jul. 11, 2019.

(51) Int. Cl.
*A61M 25/06* (2006.01)
*A61M 25/01* (2006.01)
*A61M 25/02* (2006.01)

(52) U.S. Cl.
CPC .... *A61M 25/0631* (2013.01); *A61M 25/0102* (2013.01); *A61M 25/0618* (2013.01); *A61M 2025/024* (2013.01)

(58) Field of Classification Search
CPC .......... A61M 25/0618; A61M 25/0631; A61M 25/0102; A61M 25/0625; A61M 25/0637;

(Continued)

(56) References Cited

U.S. PATENT DOCUMENTS 5,562,633 A * 10/1996 Wozencroft ...... A61M 25/0618
604/171
5,584,809 A * 12/1996 Gaba ................. A61M 25/0618
604/110

(Continued)

FOREIGN PATENT DOCUMENTS

EP     0554841        8/1993
FR     2867083 A1 *  9/2005   ........ A61M 25/0618

(Continued)

*Primary Examiner* — Rebecca E Eisenberg
*Assistant Examiner* — Adam J. Cermak
(74) *Attorney, Agent, or Firm* — Kirton McConkie; Whitney Blair; Kevin Stinger

(57) ABSTRACT

A catheter system may include a needle assembly coupled to a catheter adapter. The needle assembly may include a housing, an introducer needle, a proximal opening, a distal opening, and a needle tip shield feature. A distal tip of the introducer needle may be configured to be proximally withdrawn from a first position to a second position in which a bump feature of the introducer needle contacts and is prevented from moving through the proximal opening. In response to withdrawal of the distal tip proximally from the second position to a third position, the housing may move proximally, and the needle tip shield feature may be released to block the distal opening. The needle tip shield feature may not contact the introducer needle when the distal tip moves proximally from the first position to the second position and from the second position to the third position, which may reduce a friction-based drag force on the introducer needle.

8 Claims, 17 Drawing Sheets

(58) Field of Classification Search
CPC .......... A61M 2005/325; A61M 5/3273; A61M 5/3275
See application file for complete search history.

(56) References Cited

U.S. PATENT DOCUMENTS

| | | | | |
|---|---|---|---|---|
| 5,697,907 | A * | 12/1997 | Gaba | A61M 5/3205 604/110 |
| 6,749,588 | B1 * | 6/2004 | Howell | A61M 5/3273 604/110 |
| 7,740,614 | B2 * | 6/2010 | Murashita | A61M 25/0637 604/164.08 |
| 8,585,650 | B2 | 11/2013 | Carrez et al. | |
| 2004/0078003 | A1 * | 4/2004 | Smith | A61M 5/3275 604/164.08 |
| 2004/0092889 | A1 * | 5/2004 | Ferguson | A61M 25/0618 604/263 |
| 2005/0096592 | A1 * | 5/2005 | Carlyon | A61M 25/0618 604/110 |
| 2007/0270754 | A1 | 11/2007 | Soderholm et al. | |
| 2008/0065015 | A1 | 3/2008 | Fiser et al. | |
| 2009/0163861 | A1 * | 6/2009 | Carlyon | A61M 25/0606 604/110 |
| 2011/0282280 | A1 * | 11/2011 | Fiser | A61M 5/3273 604/110 |
| 2013/0030370 | A1 * | 1/2013 | Walker | A61M 25/0618 604/164.08 |
| 2013/0317426 | A1 * | 11/2013 | Fiser | A61M 5/3273 604/110 |
| 2014/0276468 | A1 * | 9/2014 | Kuehn | A61M 25/0618 604/263 |
| 2014/0364809 | A1 * | 12/2014 | Isaacson | A61M 25/0606 604/164.08 |
| 2015/0051584 | A1 * | 2/2015 | Korkuch | A61M 25/0606 604/510 |
| 2016/0354539 | A1 * | 12/2016 | Tan | A61M 5/1626 |
| 2018/0289932 | A1 * | 10/2018 | Isaacson | A61M 5/3273 |
| 2019/0192825 | A1 | 6/2019 | Neoh | |
| 2019/0314615 | A1 * | 10/2019 | Johnson | A61M 25/0606 |

FOREIGN PATENT DOCUMENTS

| | | | |
|---|---|---|---|
| GB | 2508466 | 6/2014 | |
| WO | WO-02076526 A2 * | 10/2002 | ........ A61M 25/0625 |
| WO | 2007/142746 | 12/2007 | |
| WO | 2011/138746 | 11/2011 | |
| WO | 2012/139034 | 10/2012 | |
| WO | WO-2016133138 A1 * | 8/2016 | ............ A61M 5/158 |
| WO | WO-2017214110 A1 * | 12/2017 | ........ A61M 25/0631 |

* cited by examiner

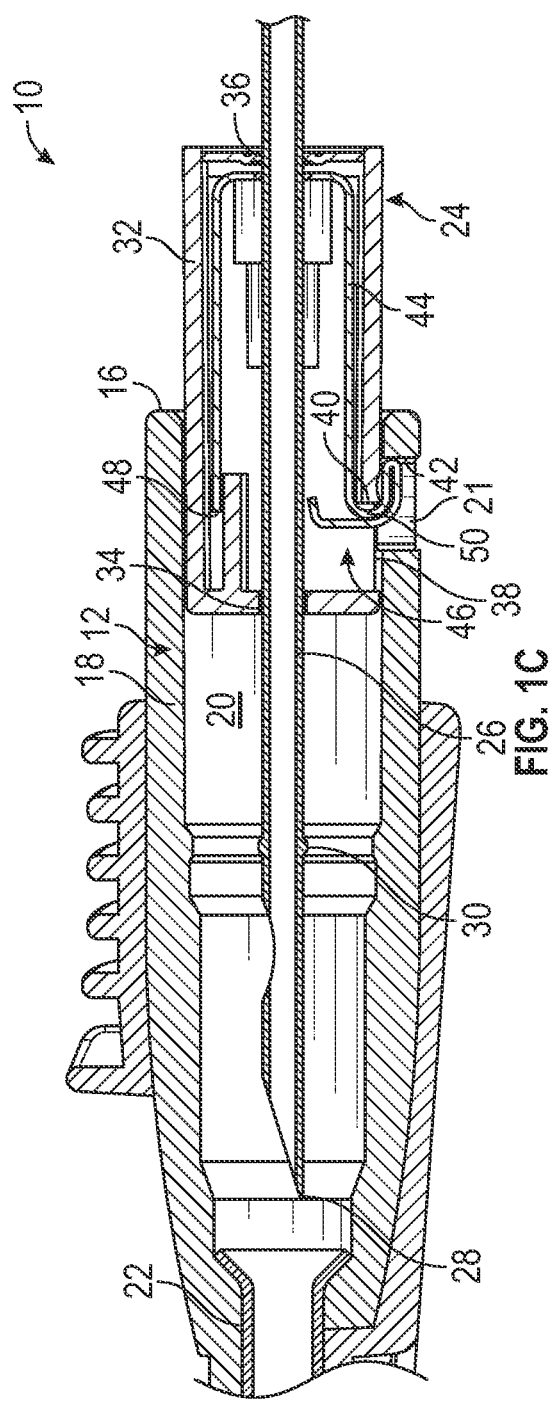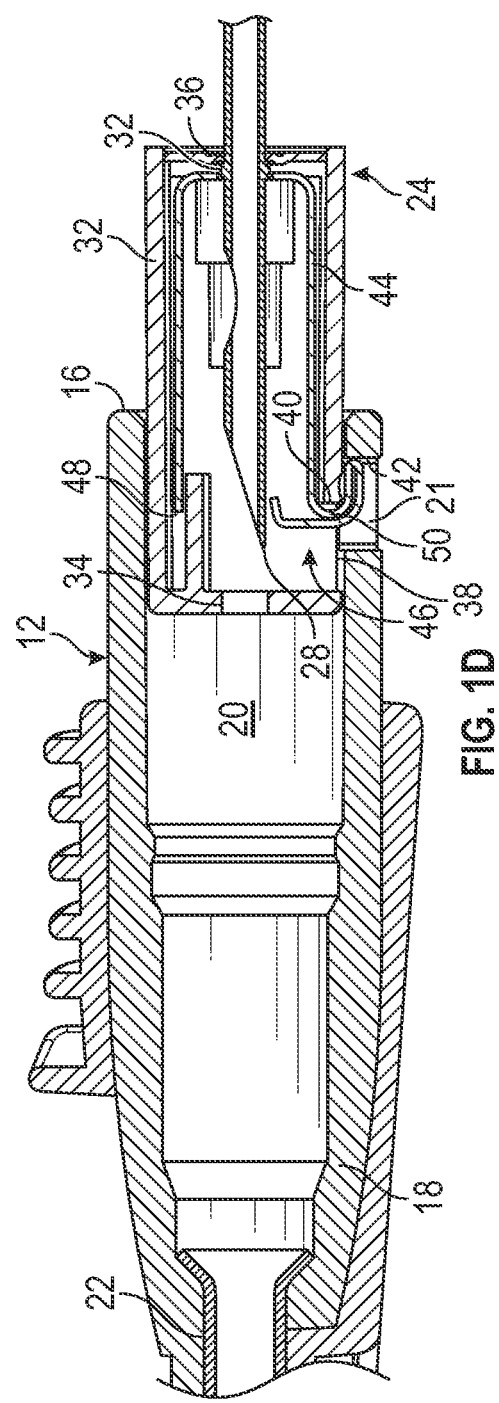

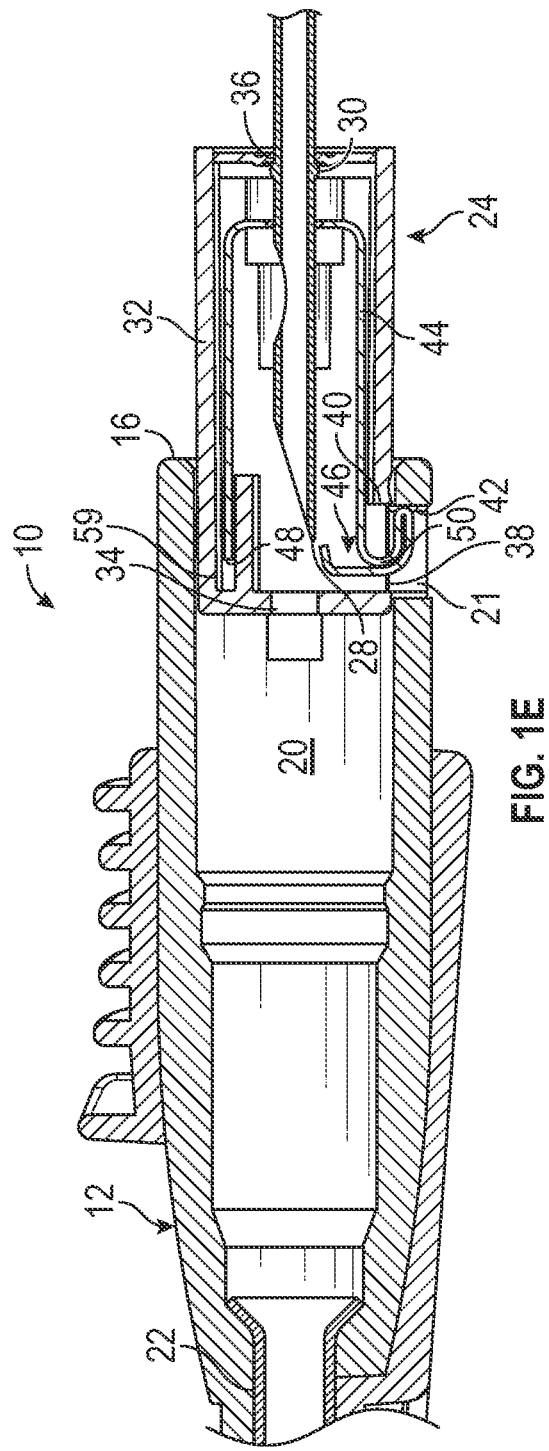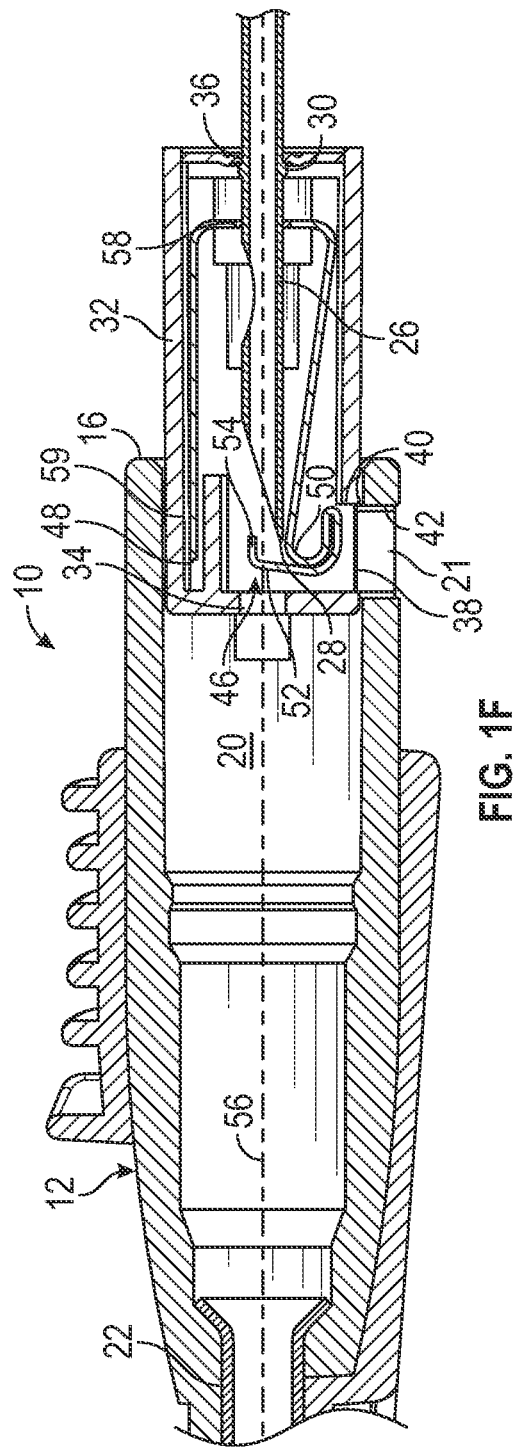

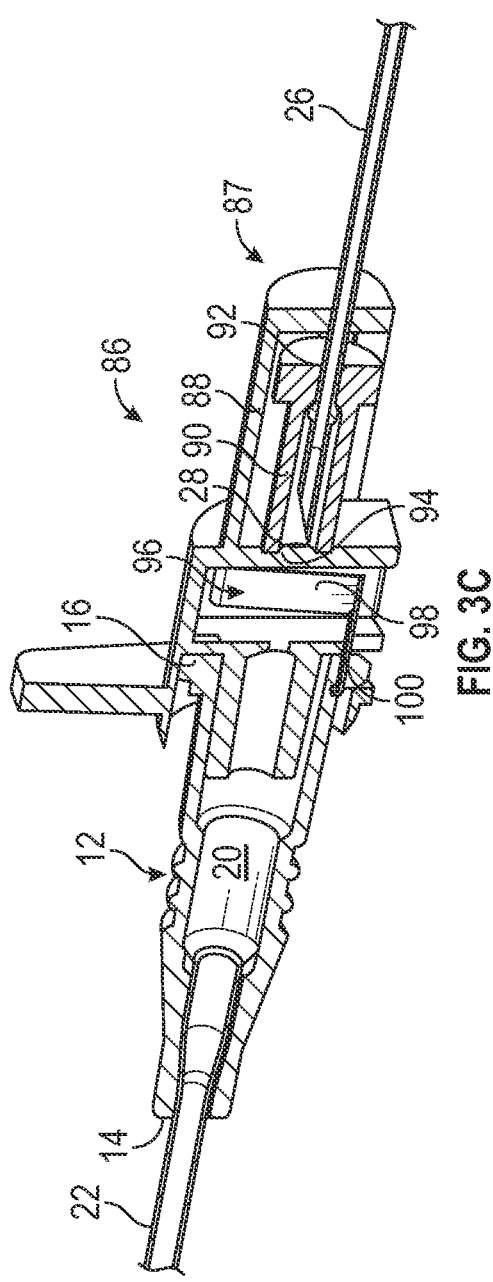
FIG. 3C
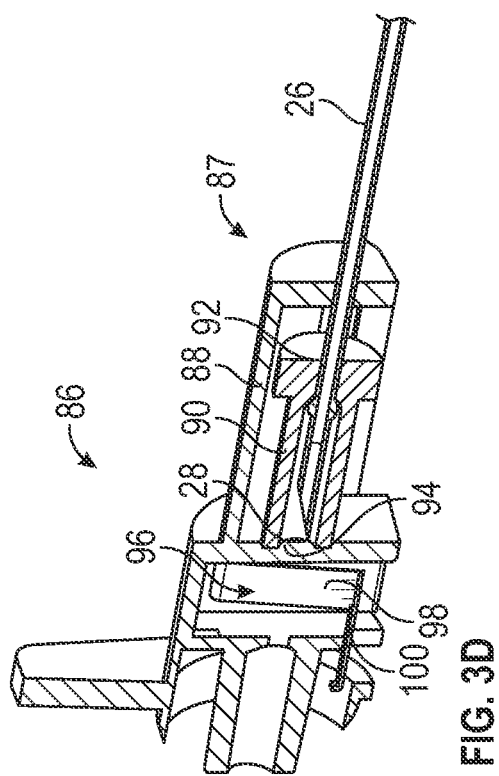
FIG. 3D
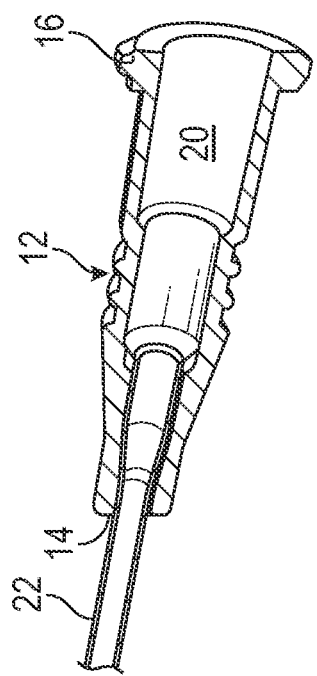

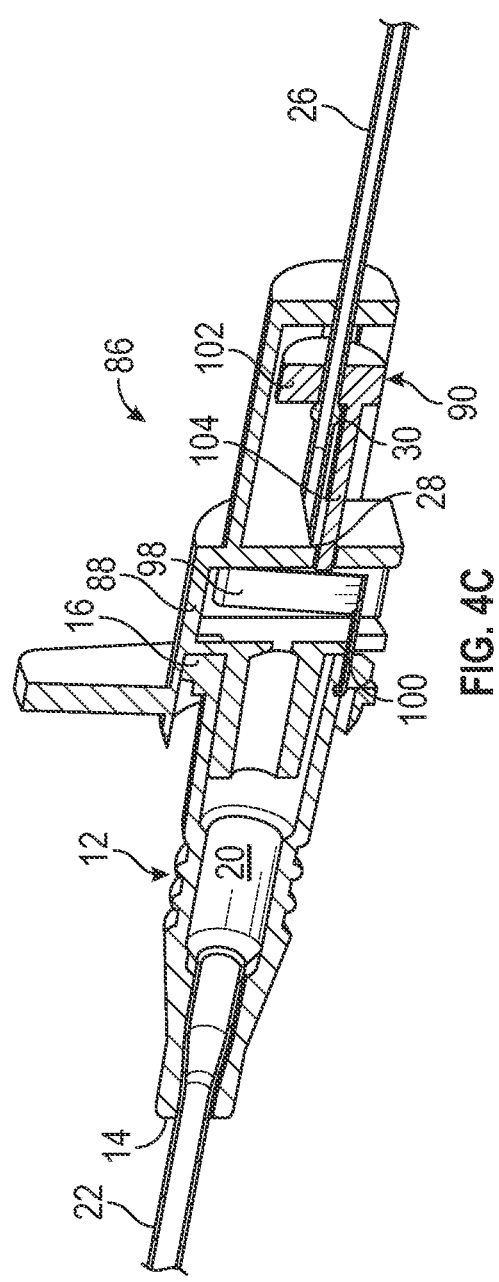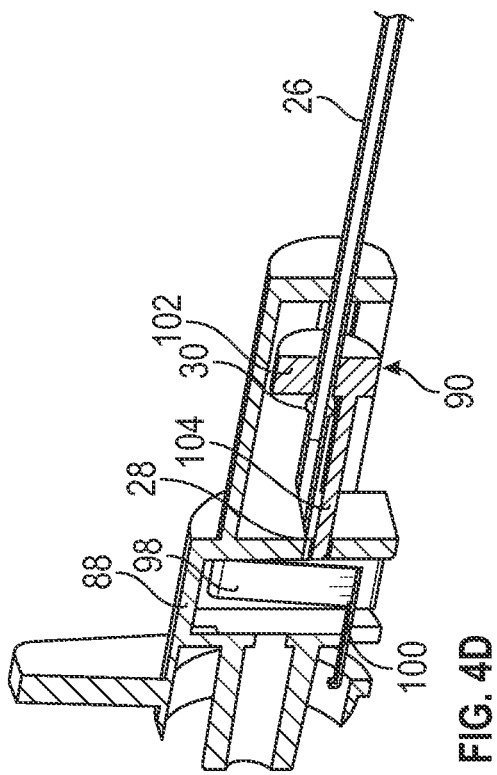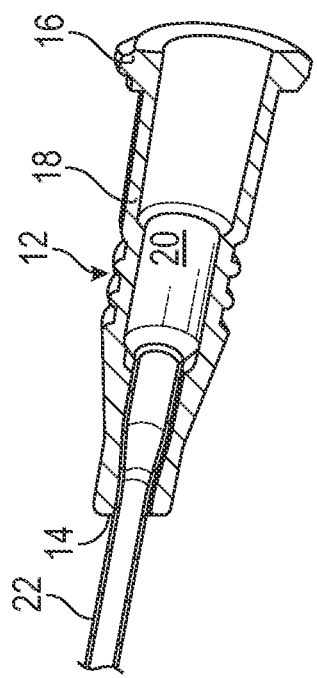
FIG. 4C
FIG. 4D

CATHETER SYSTEM FACILITATING REDUCED DRAG FORCE

RELATED APPLICATIONS

This application claims the benefit of U.S. Provisional Patent Application No. 62/873,088, filed Jul. 11, 2019 and entitled CATHETER SYSTEM FACILITATING REDUCED DRAG FORCE which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient. Once placement of the needle within the vasculature has been confirmed, the user may temporarily occlude flow in the vasculature and withdraw the needle, leaving the intravenous catheter in place for future blood withdrawal and/or fluid infusion.

When the needle is withdrawn from the intravenous catheter, clinician safety is a major concern. Not only is there a risk of needle-stick injury, the clinician wants to avoid any blood exposure from the needle. Competing for the clinician's desire for safety is a desire to maintain the intravenous catheter within the vasculature of the patient during withdrawal of the needle. Friction-based drag force as the needle is withdrawn from the intravenous catheter may lead to dislodgement of the catheter from the insertion site. Due to the friction-based drag force, the clinician may somewhat awkwardly hold the intravenous catheter in place while trying to withdraw the needle in a safe manner.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to catheter systems, as well as related devices and methods. In some embodiments, a catheter system may include a catheter adapter, which may include a distal end, a proximal end, and a wall forming a lumen. In some embodiments, the wall may include a slot. In some embodiments, the catheter system may include a catheter extending distally from the distal end of the catheter adapter.

In some embodiments, the catheter system may include a needle assembly coupled to the catheter adapter. In some embodiments, the needle assembly may include an introducer needle, which may include a distal tip and a bump feature. In some embodiments, the distal tip may be disposed distal to the catheter in a first position. In some embodiments, the first position may correspond to an insertion position, ready for insertion into vasculature of a patient.

In some embodiments, the needle assembly may include a housing, which may include a distal opening, a proximal opening, and a side opening. In some embodiments, a diameter of the proximal opening may be less than an outer diameter of the bump feature. In some embodiments, a proximal end of the side opening may be distal to a proximal end of the slot.

In some embodiments, the needle assembly may include a spring clip, which may be disposed within the housing. In some embodiments, the spring clip may include a first end and a second end. In some embodiments, the first end may include a U-shaped portion, which may be partially disposed within the slot. In some embodiments, the proximal end of the side opening may be disposed within the U-shaped portion to bias the U-shaped portion outwardly. In some embodiments, the U-shaped portion and/or an entirety of the spring clip may not contact the introducer needle, which may reduce a friction-based drag force on the introducer needle as the introducer needle is withdrawn.

In some embodiments, in response to withdrawal of the distal tip proximally from the first position to a second position, the bump feature may contact the proximal opening. In some embodiments, in response to withdrawal of the distal tip proximally from the second position to a third position, the housing and the proximal end of the side opening may move proximally, the U-shaped portion may be released and move inwardly, and the spring clip may block the distal opening. In some embodiments, blocking the distal opening may prevent needle stick injury. In some embodiments, the first end of the spring clip may abut the proximal end of the side opening, which may prevent the spring clip from moving distally in response to the withdrawal of the distal tip proximally from the second position to the third position.

In some embodiments, the first end of the spring clip may include a shield portion. In some embodiments, the shield portion may be generally L-shaped and may extend from the U-shaped portion. In some embodiments, in response to withdrawal of the distal tip proximally from the second position to the third position, the shield portion may block the distal opening.

In some embodiments, the first end of the spring clip may include a lip, which may extend proximally from the shield portion. In some embodiments, the shield portion may be disposed in between the lip and the U-shaped portion. In some embodiments, in response to withdrawal of the distal tip proximally from the second position to the third position, the distal tip may be disposed between the lip and the U-shaped portion.

In some embodiments, the spring clip may include an opening. In some embodiments, the introducer needle may extend through the opening of the spring clip. In some embodiments, the spring clip is spaced apart from the opening, which may reduce a friction-based drag force on the introducer needle as the introducer needle is withdrawn. In some embodiments, an outer diameter of the introducer needle proximal to the bump feature may be slightly less than the proximal opening of the housing such that the introducer needle contacts and is supported by the proximal opening. In these embodiments, a close fit between the introducer needle and the proximal opening of the housing may prevent blood leakage through the proximal opening of the housing.

In some embodiments, the spring clip may be generally U-shaped between the first end and the second end. In some embodiments, the opening of the spring clip may be disposed within a mouth of a general U-shape between the first end and the second end. In some embodiments, the mouth of the general U-shape between the first end and the second end may face in a distal direction, and a mouth of the U-shaped portion may face in a proximal direction.

In some embodiments, the housing may include a groove. In some embodiments, the second end of the spring clip may be disposed within the groove. In some embodiments, in response to withdrawal of the distal tip proximally from the second position to the third position, the housing and the proximal end of the side opening may move proximally and the second end of the spring clip may move closer to a distal end of the groove.

In some embodiments, the housing may include one or more support ledges, which may be disposed lateral to the introducer needle. In some embodiments, the needle assembly may include a needle tip shield, which may include one or more contact surfaces. In some embodiments, the needle tip shield may include an elongated body with one or more arms extending inwardly from the elongated body. In some embodiments, the arms may include the contact surfaces. In some embodiments, the needle tip shield may not contact the introducer needle, which may reduce a friction-based drag force on the introducer needle as the introducer needle is withdrawn.

In some embodiments, a compression element may be disposed at least partially around the housing and the needle tip shield. In some embodiments, the contact surfaces may be aligned with the support ledges and the compression element may press the contact surfaces against the support ledges. In some embodiments, in response to withdrawal of the distal tip proximally from the second position to the third position, the housing may move proximally and the contact surfaces may be unaligned with the support ledges such that the compression element moves the housing and the needle tip shield together and the needle tip shield blocks the distal opening.

In some embodiments, the wall may include a slot. In some embodiments, the needle tip shield may include a protrusion disposed within the slot. In some embodiments, in response to withdrawal of the distal tip proximally from the second position to the third position, the housing may move proximally and the contact surfaces may be unaligned with the support ledges such that the compression element moves the housing and the needle tip shield together and the protrusion is removed from the slot. In some embodiments, in response to the protrusion being removed from the slot, the catheter adapter and the needle assembly may be uncoupled.

In some embodiments, the housing may include an outer housing. In some embodiments, the needle assembly may include a bias element disposed within the housing. In some embodiments, the bias element may include a proximal opening, which may include a diameter less than the outer diameter of the bump feature. In some embodiments, the introducer needle may extend through the distal opening of the housing and the proximal opening of the bias element.

In some embodiments, the needle assembly may include another spring clip, which may be disposed within the housing. In some embodiments, the spring clip may include a U-shaped portion and an arm that extends distal to the U-shaped portion. In some embodiments, the arm may be engaged with the catheter adapter. In some embodiments, the bias element may contact the U-shaped portion to bias the spring clip in a compressed position.

In some embodiments, the distal tip may be configured to be withdrawn proximally from the first position to a particular second position in which the bump feature contacts the proximal opening of the bias element. In some embodiments, in response to withdrawal of the distal tip proximally from the second position to a particular third position, the bias element may move proximal to the U-shaped portion to release the U-shaped portion from the compressed position and the arm from the catheter adapter, and the U-shaped portion may block the distal opening such that the distal tip of the introducer needle is prevented from exiting the distal opening.

In some embodiments, the bias element may include an inner housing, which may surround the introducer needle. In some embodiments, the bias element may include a base and an extension extending distally from the base. In some embodiments, the extension may contact the U-shaped portion to bias the spring clip in the compressed position. In some embodiments, the base may include the proximal opening of the bias element. In some embodiments, the extension is spaced apart from the introducer needle. In some embodiments, the extension may include a rod. In some embodiments, the housing may include an inner support wall. In some embodiments, the extension may extend through the inner support wall and may be slidable through the inner support wall.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1C is a cross-sectional view of a portion of the catheter system of FIG. 1A, illustrating an example needle assembly, according to some embodiments;

FIG. 1D is a cross-sectional view of a portion of the catheter system of FIG. 1A, illustrating the distal tip in an example second position, according to some embodiments;

FIG. 1E is a cross-sectional view of a portion of the catheter system of FIG. 1A, illustrating the distal tip in an example third position, according to some embodiments;

FIG. 1F is a cross-sectional view of a portion of the catheter system of FIG. 1A, illustrating the distal tip in the third position and an example spring clip blocking a distal opening of the needle assembly in response to movement of the distal tip from the second position to the third position, according to some embodiments;

FIG. 3C is a cross-sectional view of a portion of the catheter system of FIG. 3A, illustrating the distal tip in a third position, according to some embodiments;

FIG. 3D is a cross-sectional view of a portion of the catheter system of FIG. 3A, illustrating the needle assembly removed from an example catheter adapter, according to some embodiments;

FIG. 4C is a cross-sectional view of a portion of the catheter system of FIG. 3A, illustrating the distal tip in the third position and the other bias element, according to some embodiments;

FIG. 4D is a cross-sectional view of a portion of the catheter system of FIG. 3A, illustrating other bias element and the needle assembly removed from the catheter adapter, according to some embodiments;

DESCRIPTION OF EMBODIMENTS

In some embodiments, the present disclosure relates to a catheter system, which may include a needle assembly coupled to a catheter adapter. The needle assembly may include a housing, an introducer needle, a proximal opening, a distal opening, and a needle tip shield feature. A distal tip of the introducer needle may be configured to be proximally withdrawn from a first position to a second position in which a bump feature of the introducer needle contacts and is prevented from moving through the proximal opening. In response to withdrawal of the distal tip proximally from the second position to a third position, the housing may move proximally, and the needle tip shield feature may be released to block the distal opening. The needle tip shield feature may not contact the introducer needle when the distal tip moves proximally from the first position to the second position and from the second position to the third position, which may reduce a friction-based drag force on the introducer needle. FIGS. 1-4 further describe examples of the catheter system, according to some embodiments.

Figure 1A:
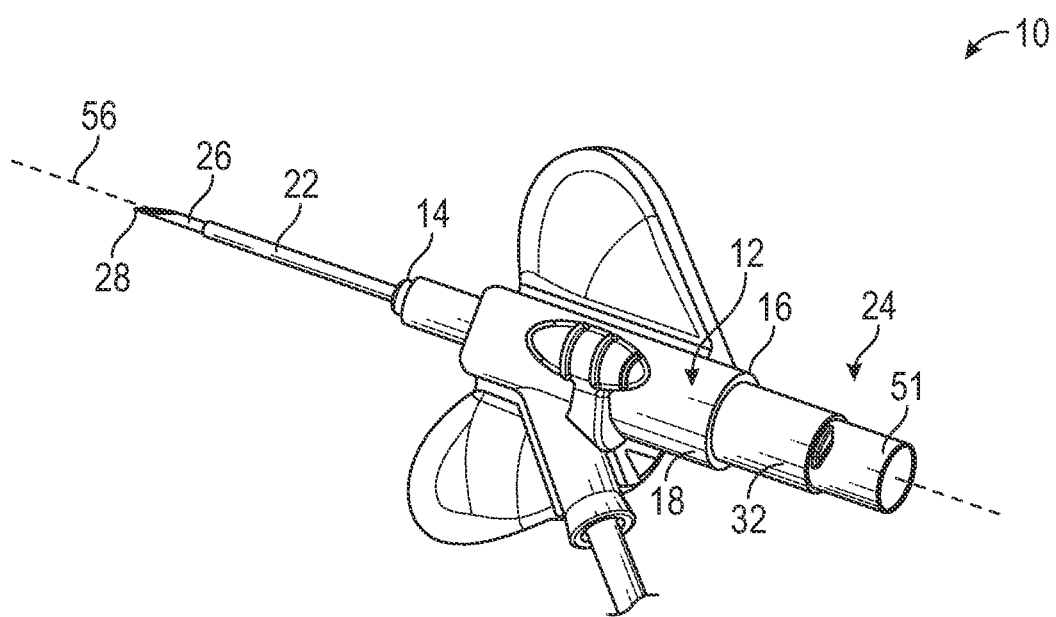
FIG. 1A is an upper perspective view of an example catheter system, according to some embodiments.
Figure 1B:
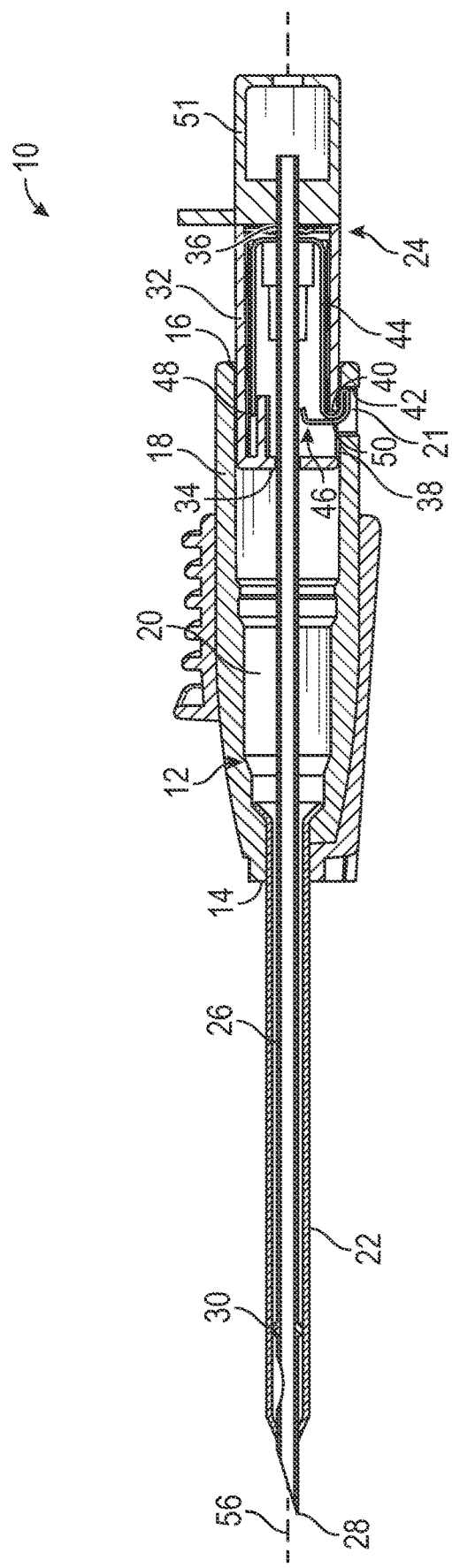
FIG. 1B is a cross-sectional view of the catheter system of FIG. 1A, illustrating an example introducer needle that includes an example distal tip in an example first position, according to some embodiments.

Referring now to FIGS. 1A-1B, a catheter system 10 is illustrated, according to some embodiments. In some embodiments, the catheter system 10 may include a catheter adapter 12, which may include a distal end 14, a proximal end 16, and a wall 18 forming a lumen 20. In some embodiments, the lumen 20 may extend through the distal end 14 and the proximal end 16. In some embodiments, the wall 18 may include a slot 21. In some embodiments, the slot 21 may include a hole extending through the wall 18 or a groove.

In some embodiments, the catheter system 10 may include a catheter 22 extending distally from the distal end 14 of the catheter adapter 12. In some embodiments, the catheter 22 may include a peripheral intravenous catheter ("PIVC"), a midline catheter, a peripherally inserted central catheter ("PICC"), or another suitable catheter. In some embodiments, the catheter system 10 may include any suitable catheter adapter 12. In some embodiments, the catheter adapter 12 may include a side port in fluid communication with the lumen 20 of the catheter adapter 12. In some embodiments, an extension tube may be integrated within the side port and may be part of an extension set. In some embodiments, the catheter adapter 12 may be straight or non-integrated and may not include the extension tube.

In some embodiments, the catheter system 10 may include a needle assembly 24 coupled to the catheter adapter 12. In some embodiments, the needle assembly 24 may include an introducer needle 26, which may include a distal tip 28 and an optional bump feature 30. In some embodiments, the introducer needle 26 may be constructed of metal and the distal tip 28 may be sharp. In some embodiments, the distal tip 28 may be disposed distal to the catheter 22 in a first position, as illustrated, for example, in FIGS. 1A-1B. In some embodiments, the first position may correspond to an insertion position, ready for insertion into vasculature of a patient.

In some embodiments, the needle assembly 24 may include a housing 32, which may include a distal opening 34, a proximal opening 36, and a side opening 38. In some embodiments, a diameter of the proximal opening 36 may be less than an outer diameter of the bump feature 30 such that the bump feature 30 may not pass through the proximal opening 36. In some embodiments, the bump feature 30 may include any suitable feature having an increased outer diameter. In some embodiments, a proximal end of the housing 32 may include a washer, which may include the proximal opening 36.

In some embodiments, a proximal end 40 of the side opening 38 may be distal to a proximal end 42 of the slot 21. In some embodiments, the needle assembly 24 may include a spring clip 44, which may be disposed within the housing 32. In some embodiments, the spring clip 44 may include a first end 46 and a second end 48. In some embodiments, the first end 46 may include a U-shaped portion 50, which may be partially disposed within the slot 21. In some embodiments, the proximal end of the side opening 38 may be disposed within the U-shaped portion 50 to bias and hold the U-shaped portion 50 outwardly. In some embodiments, the U-shaped portion 50 and/or an entirety of the spring clip 44 may not contact the introducer needle 26, which may reduce a friction-based drag force on the introducer needle 26 as the introducer needle 26 is withdrawn.

In some embodiments, the U-shaped portion 50 may be generally U-shaped, which may include a V-shape or another bend shape that is suitable for retaining the proximal end 40 of the side opening 38 when the distal tip 28 is in the first position and the second position. In some embodiments, the U-shaped portion may include a 180° bend. In some embodiments, the spring clip 44 may be constructed of metal or another suitable material. In some embodiments, the spring clip 44 may be resilient.

In some embodiments, a proximal end of the introducer needle 26 may be secured within a needle hub 51. In some embodiments, the needle hub 51 may be proximate the housing 32. In some embodiments, the needle hub 51 may include one or more grip features, which may facilitate gripping and movement of the needle hub 51 in a proximal direction by the clinician to withdraw the introducer needle 26 from the vasculature of the patient and the catheter 22.

Referring now to FIG. 1C, the distal tip 28 is illustrated between the first position and a second position. Referring now to FIG. 1D, in some embodiments, in response to withdrawal of the distal tip 28 proximally from the first position to the second position, illustrated, for example, in FIG. 1C, the bump feature 30 may contact the proximal opening 36.

Referring now to FIGS. 1E-1F, in some embodiments, in response to withdrawal of the distal tip 28 proximally from the second position to a third position, illustrated, for example, in FIG. 1E, the housing 32 and the proximal end 40 of the side opening 38 may move proximally, the U-shaped portion 50 may be released and move inwardly, and the spring clip 44 may block the distal opening 34. In some embodiments, the first end 46 of the spring clip 44 may abut the proximal end 40 of the side opening 38, which may prevent the spring clip 44 from moving proximally in response to the withdrawal of the distal tip 28 proximally from the second position to the third position. In some embodiments, the distal tip 28 and the housing 32 may move approximately 1 mm or another suitable distance between the first position and the second position, which may facilitate ease of withdrawal and capture of the distal tip 28.

Referring now to FIG. 1F, in some embodiments, the first end of the spring clip 44 may include a needle tip shield feature or a shield portion 52. In some embodiments, the shield portion 52 may be generally L-shaped and may extend from the U-shaped portion 50. In some embodiments, in response to withdrawal of the distal tip 28 proximally from the second position to the third position, the shield portion 52 may block the distal opening 34 such that the distal tip 28 is prevented from exiting the distal opening 34. In some embodiments, the spring clip 44 or the shield portion 52 may also prevent blood from leaking out of the distal opening 34.

In some embodiments, the first end 46 of the spring clip 44 may include a lip 54, which may extend proximally from the shield portion 52. In some embodiments, the shield portion 52 may be disposed in between the lip 54 and the U-shaped portion 50. In some embodiments, in response to withdrawal of the distal tip 28 proximally from the second position to the third position, the distal tip 28 may be disposed between the lip 54 and the U-shaped portion 50. In these embodiments, the first end 46 of the spring clip 44 may cross a longitudinal axis 56 (see also FIGS. 1A-1B) of the catheter system 10.

In some embodiments, the spring clip 44 may include an opening 58. In some embodiments, the introducer needle 26 may extend through the opening 58 of the spring clip 44. In some embodiments, the introducer needle may be spaced apart from opening 58, which may reduce a friction-based drag force on the introducer needle 26 as the introducer needle 26 is withdrawn proximally. In some embodiments, an outer diameter of the introducer needle 26 proximal to the bump feature 30 may be slightly less than the proximal opening 36 of the housing 32 such that the introducer needle contacts and is supported by the proximal opening 36. In these embodiments, a close fit between the introducer needle 26 and the proximal opening 36 of the housing 32 may prevent blood leakage through the proximal opening 36 of the housing 32.

In some embodiments, the spring clip 44 may be generally U-shaped between the first end 46 and the second end 48. In some embodiments, the opening 58 of the spring clip 44 may be disposed within a mouth of a general U-shape between the first end 46 and the second end 48. In some embodiments, the mouth of the general U-shape between the first end 46 and the second end 48 may face in a distal direction, and a mouth of the U-shaped portion 50 may face in a proximal direction.

In some embodiments, the housing 32 may include a groove 59. In some embodiments, the second end 48 of the spring clip 44 may be disposed within the groove 59. In some embodiments, in response to withdrawal of the distal tip 28 proximally from the second position to the third position, the housing 32 and the proximal end 40 of the side opening 38 may move proximally and the second end 48 of the spring clip 44 may move closer to a distal end of the groove 59.

Figure 1G:
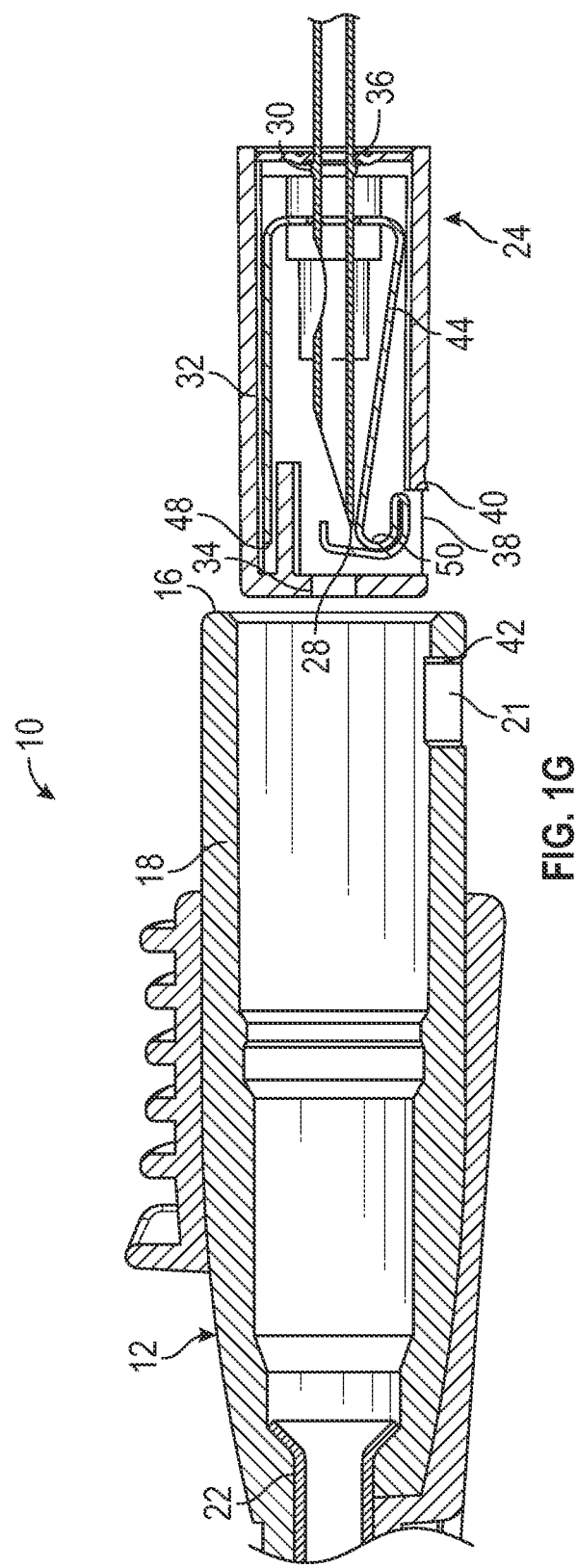
FIG. 1G is a cross-sectional view of a portion of the catheter system of FIG. 1A, illustrating the needle assembly removed from an example catheter adapter, according to some embodiments.
Figure 1H:
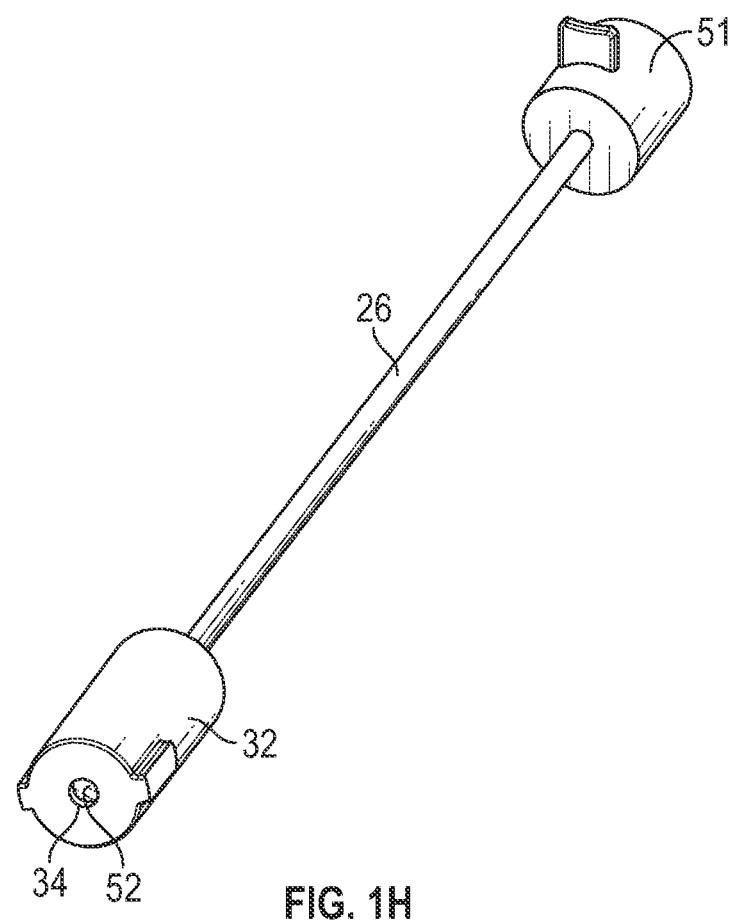
FIG. 1H is an upper perspective view of the needle assembly, according to some embodiments.

Referring now to FIGS. 1G-1H, in some embodiments, the needle assembly 24 may be removed from the catheter adapter 12 in response to proximally withdrawing the distal tip 28 from the second position to the third position and release of the U-shaped portion from the proximal end 40 of the side opening 38 and the slot 21.

Figure 2A:
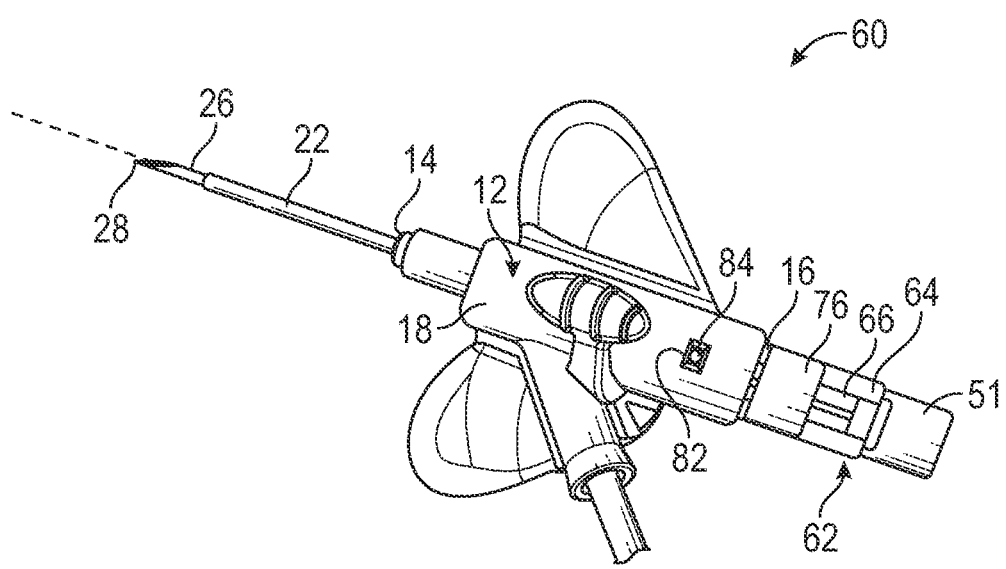
FIG. 2A is an upper perspective view of another example catheter system, according to some embodiments.
Figure 2B:
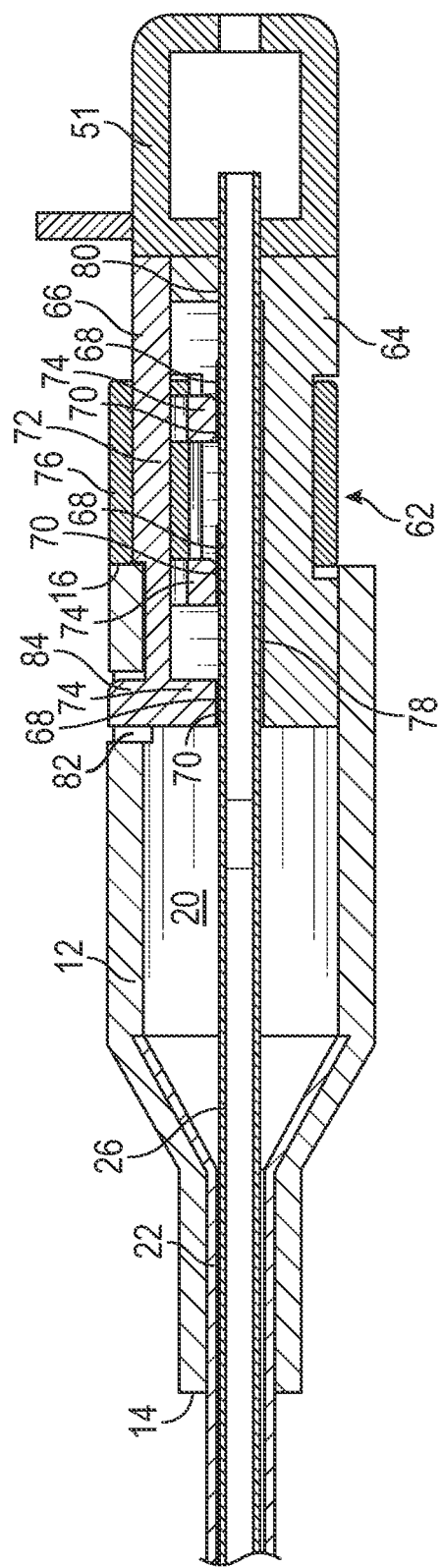
FIG. 2B is a cross-sectional view of the catheter system of FIG. 2A, illustrating an example introducer needle that includes an example distal tip in an example first position, according to some embodiments.

Referring now to FIGS. 2A-2B, a catheter system 60 is illustrated, according to some embodiments. In some embodiments, the catheter system 60 may include or correspond to the catheter system 10. In some embodiments, the catheter system 60 may be similar or identical to the catheter system 10 of FIGS. 1A-1H in terms of one or more included components and/or operation. FIGS. 2A-2B illustrate the distal tip 28 of the introducer needle 26 in a first position, according to some embodiments.

In some embodiments, a needle assembly 62 of the catheter system 60 may include a housing 64, which may include or correspond to the housing 32 of FIGS. 1A-1H, and a needle tip shield 66. In some embodiments, the housing 64 may include one or more support ledges 68, which may be disposed lateral to the introducer needle 26. In some embodiments, the needle tip shield 66 may include one or more contact surfaces 70. In some embodiments, the needle tip shield 66 may include an elongated body 72 with one or more arms 74 extending inwardly from the elongated body 72. In some embodiments, the arms 74 may include the contact surfaces 70. In some embodiments, the arms 74 may be lateral to the introducer needle 26 and may not contact the introducer needle 26. In some embodiments, the needle tip shield 66 may not contact the introducer needle 26, as illustrated, for example, in FIG. 2B, which may reduce a friction-based drag force on the introducer needle 26 as the introducer needle 26 is withdrawn.

In some embodiments, a compression element 76 may be disposed at least partially around the housing 64 and the needle tip shield 66. In some embodiments, the compression element may include a spring band, which may be annular. In some embodiments, the contact surfaces 70 may be aligned with the support ledges 68, and the compression element 76 may press the contact surfaces 70 against the support ledges 68.

In some embodiments, the housing 64 may include a distal opening 78 and a proximal opening 80. In some embodiments, a diameter of the proximal opening 80 may be less than an outer diameter of the bump feature 30 such that the bump feature 30 may not pass through the proximal opening 80. In some embodiments, a proximal end of the housing 64 may include a washer, which may include the proximal opening 80.

Figure 2C:
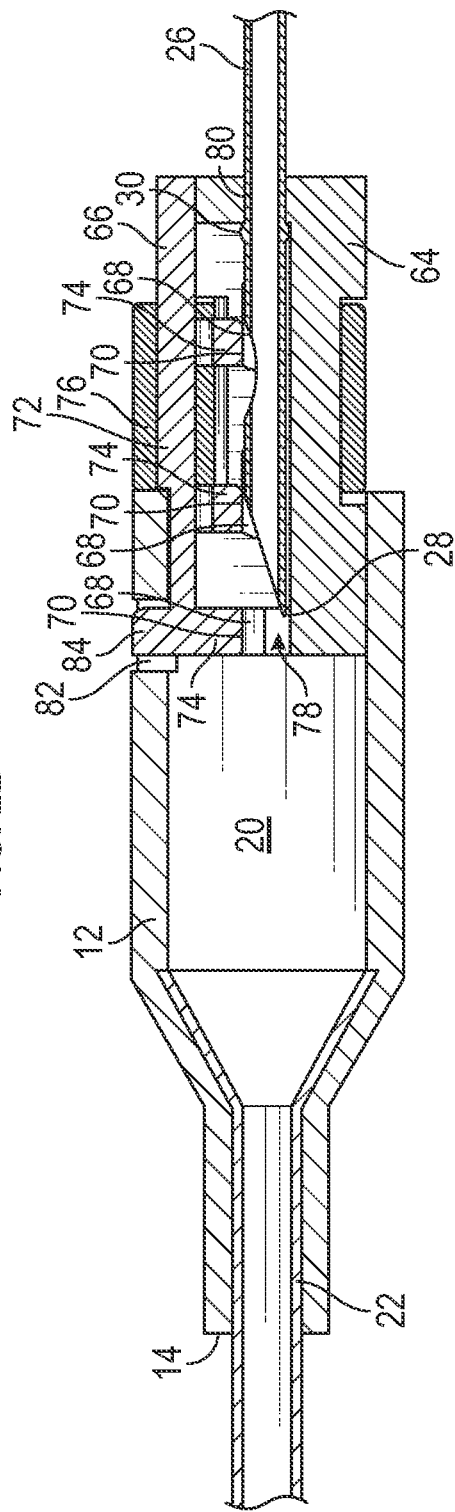
FIG. 2C is a cross-sectional view of a portion of the catheter system of FIG. 2A, illustrating the distal tip in an example second position, according to some embodiments.

Referring now to FIG. 2C, in some embodiments, in response to withdrawal of the distal tip 28 proximally from the first position to a second position, illustrated, for example, in FIG. 2C, the bump feature 30 may contact the proximal opening 80.

Figure 2D:
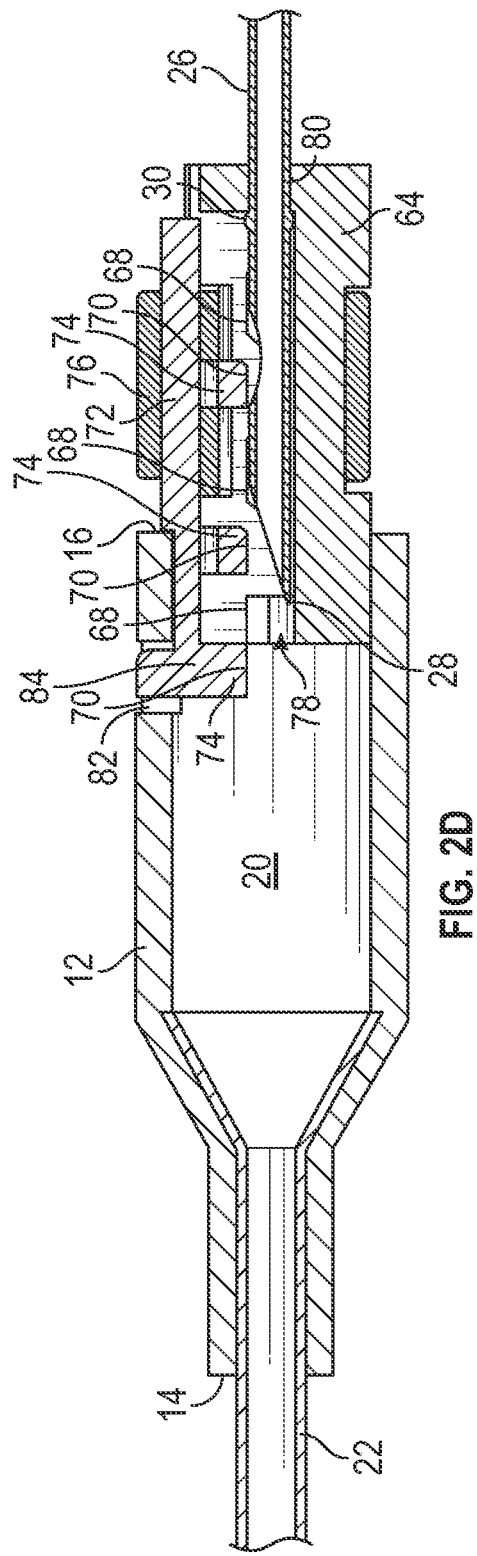
FIG. 2D is a cross-sectional view of a portion of the catheter system of FIG. 2A, illustrating the distal tip in a third position, according to some embodiments.
Figure 2E:
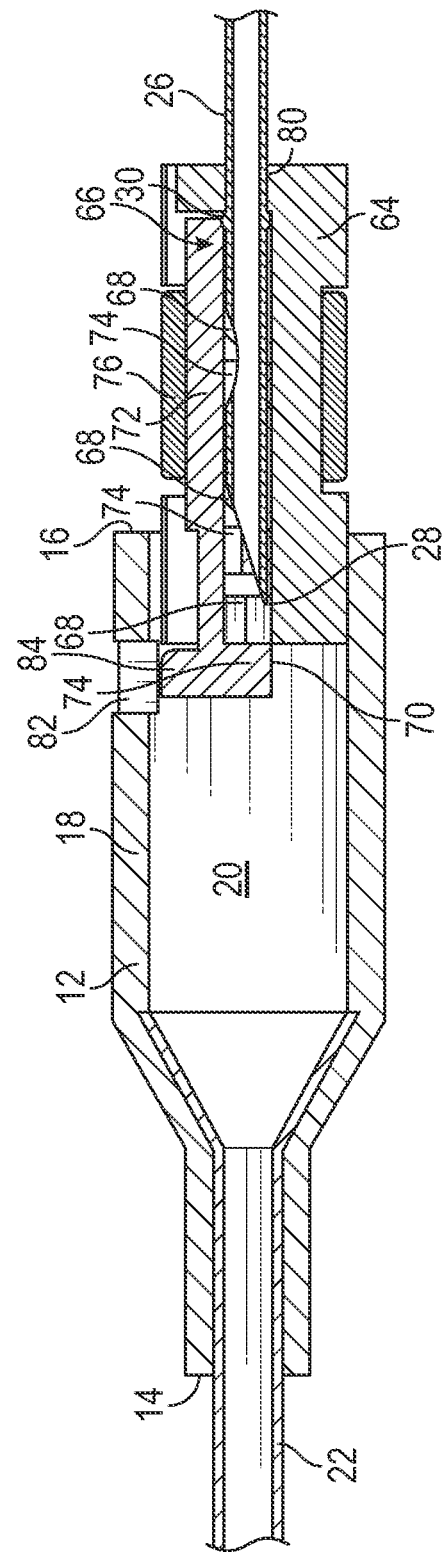
FIG. 2E is a cross-sectional view of a portion of the catheter system of FIG. 2A, illustrating the distal tip in the third position and an example needle tip shield blocking a distal opening of an example needle assembly in response to movement of the distal tip from the second position to the third position, according to some embodiments.

Referring now to FIGS. 2D-2E, in some embodiments, in response to withdrawal of the distal tip 28 proximally from the second position to a third position, illustrated, for example, in FIG. 2D, the housing 64 may move proximally and the contact surfaces 70 may be unaligned with the support ledges 68. In response, as illustrated in FIG. 2E, for example, the compression element 76 moves the housing 64 and the needle tip shield 66 together and the needle tip shield 66 blocks the distal opening 78 and/or prevents blood from leaking out of the distal opening 78.

In some embodiments, the wall 18 of the catheter adapter 12 may include a slot 82. In some embodiments, the slot 82 may include a hole extending through the wall 18 or a groove. In some embodiments, the needle tip shield 66 may include a protrusion 84 disposed within the slot 82. In some embodiments, in response to withdrawal of the distal tip 28 proximally from the second position to the third position, the housing 64 may move proximally and the contact surfaces 70 may be unaligned with the support ledges 68 such that the compression element 76 moves the housing 64 and the needle tip shield 66 together and the protrusion 84 is removed from the slot 82.

Figure 2F:
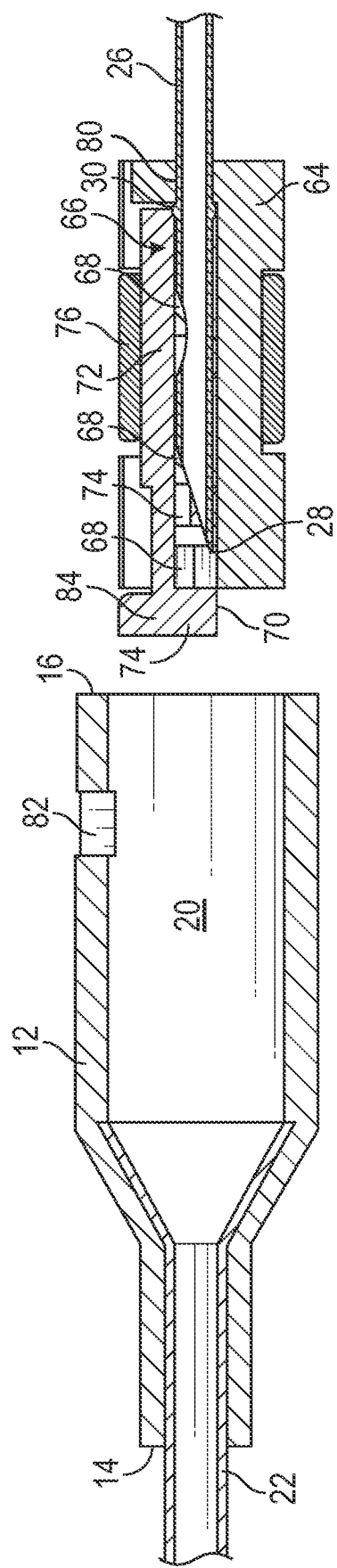
FIG. 2F is a cross-sectional view of a portion of the catheter system of FIG. 2A, illustrating the needle assembly removed from an example catheter adapter, according to some embodiments.
Figure 2G:
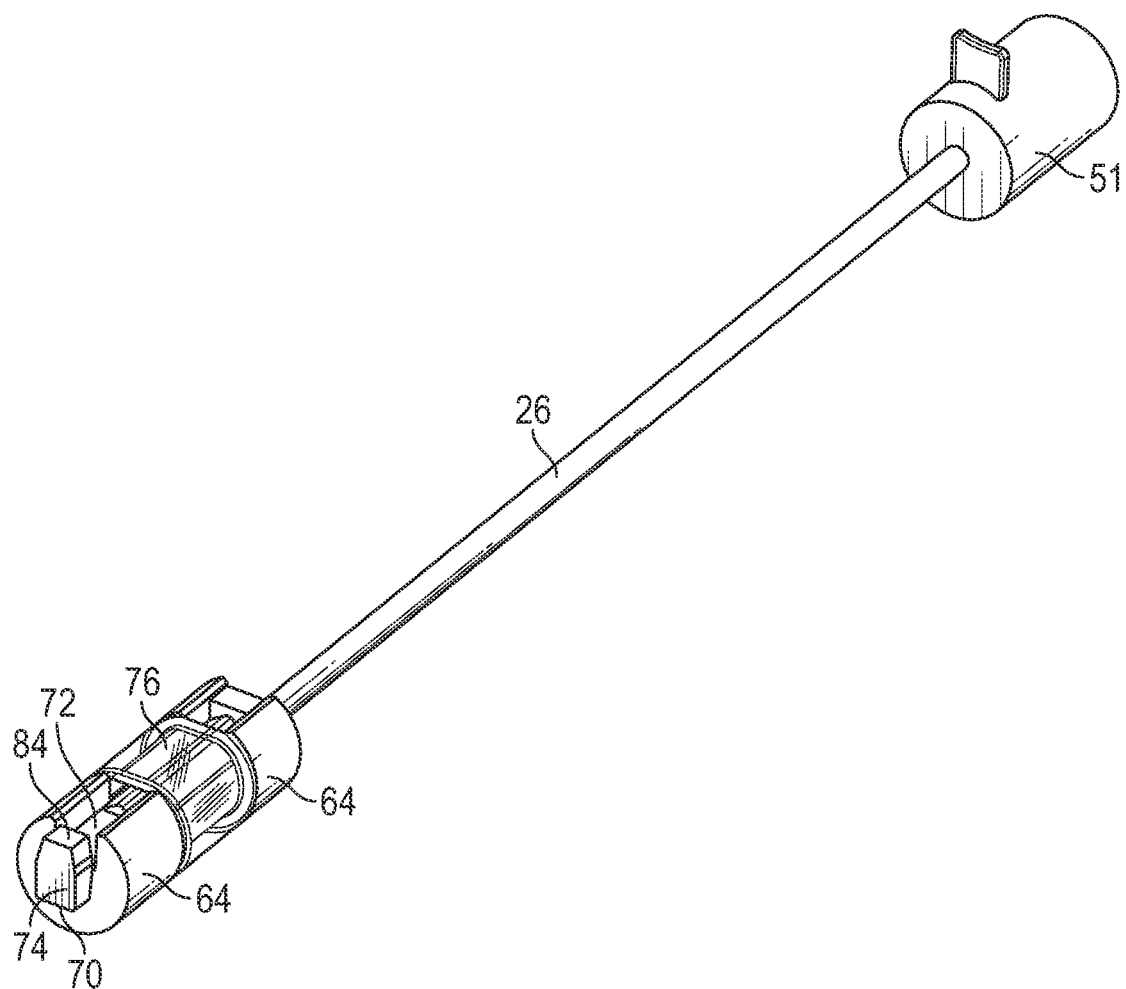
FIG. 2G is an upper perspective view of the needle assembly, according to some embodiments.

Referring now to FIGS. 2F-2G, in some embodiments, in response to the protrusion 84 being removed from the slot 82, the catheter adapter 12 and the needle assembly 62 may be uncoupled. In some embodiments, the needle assembly 24 may be removed from the catheter adapter 12 in response to proximally withdrawing the distal tip 28 from the second position to the third position and uncoupling of the catheter adapter 12 and the needle assembly 62.

Figure 3A:
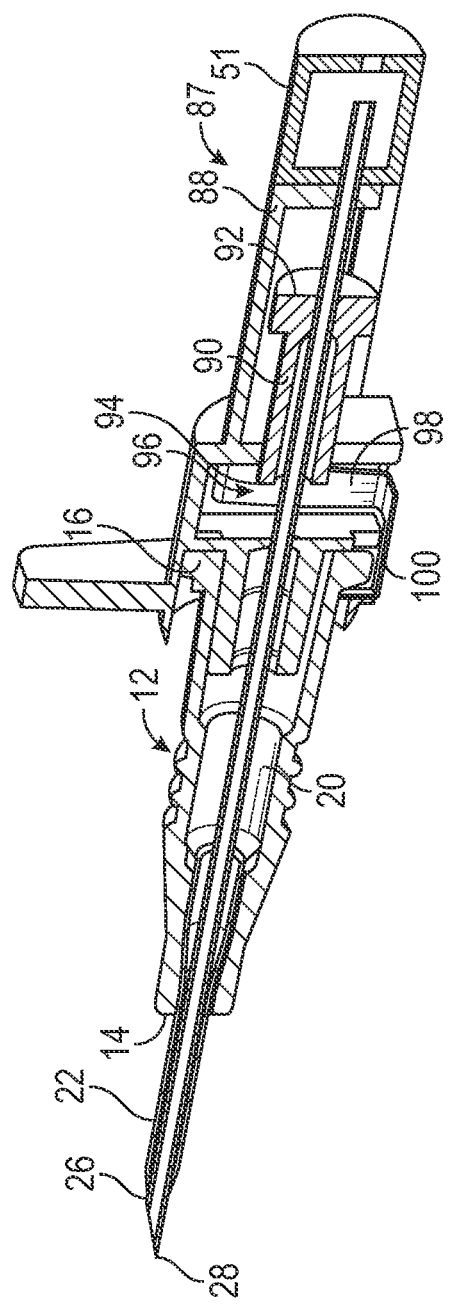
FIG. 3A is cross-sectional view of another example catheter system, illustrating an example bias element and an example introducer needle that includes an example distal tip in an example first position, according to some embodiments.

Referring now to FIG. 3A, a catheter system 86 is illustrated, according to some embodiments. In some embodiments, the catheter system 86 may include or correspond to the catheter system 10 and/or the catheter system 60. In some embodiments, the catheter system 86 may be similar or identical to the catheter system 10 of FIGS. 1A-1H and/or the catheter system 60 of FIGS. 2A-2G in terms of one or more included components and/or operation. FIG. 3A illustrates the distal tip 28 of the introducer needle 26 in a first position, according to some embodiments.

In some embodiments, the catheter system 86 may include a needle assembly 87, which may include an outer housing 88, which may include or correspond to the housing 32 of FIGS. 1A-1H and/or the housing 64 of FIGS. 2A-2G. In some embodiments, the needle assembly 87 may include a bias element 90, which may be disposed within the outer housing 88. In some embodiments, the bias element 90 may include a proximal opening 92, which may include a diameter less than the outer diameter of the bump feature 30 such that the bump feature 30 may not pass through the proximal opening 92. In some embodiments, the introducer needle 26 may extend through a distal opening 94 of the outer housing 88 and the proximal opening 92 of the bias element 90.

In some embodiments, the needle assembly 87 may include a spring clip 96, which may be disposed within the outer housing 88. In some embodiments, the spring clip 96 may include a U-shaped portion 98 and an arm 100 that extends distal to the U-shaped portion 98. In some embodiments, the arm 100 may be engaged with the catheter adapter 12. In some embodiments, an end of the arm 100 may include a finger, which may be disposed in a groove of the catheter adapter 12. In some embodiments, the bias element 90 may contact the U-shaped portion 98 to bias the spring clip 96 in a compressed position, as illustrated, for example in FIG. 3A-3B.

Figure 3B:
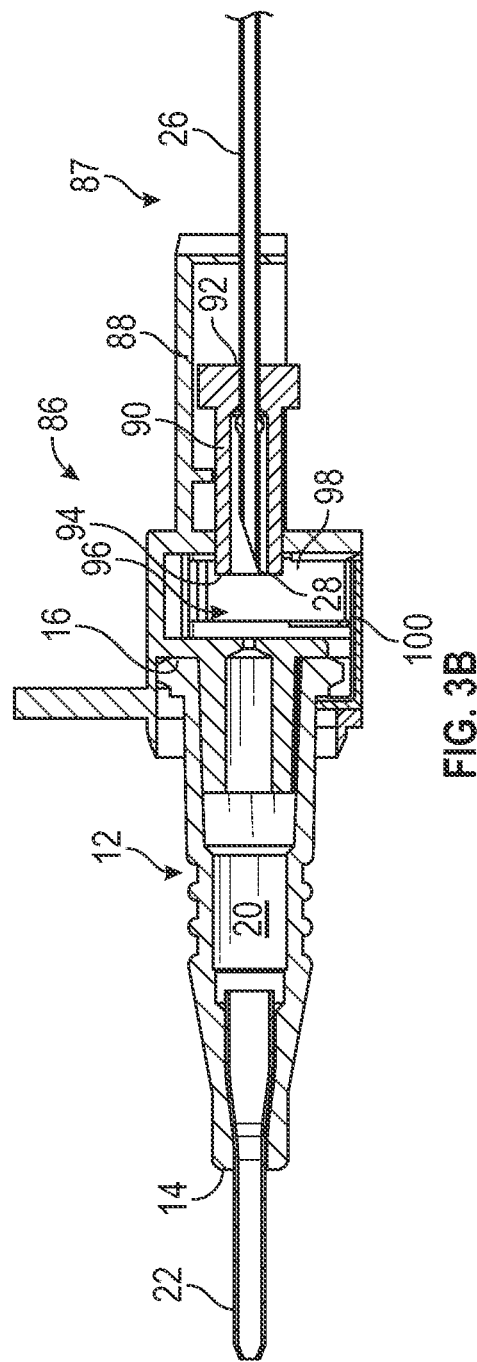
FIG. 3B is a cross-sectional view of a portion of the catheter system of FIG. 3A, illustrating the distal tip in an example second position, according to some embodiments.

Referring now to FIG. 3B, in some embodiments, the distal tip 28 may be configured to be withdrawn proximally from the first position to a second position in which the bump feature 30 contacts the proximal opening 92 of the bias element 90.

Referring now to FIG. 3C, in some embodiments, in response to withdrawal of the distal tip 28 proximally from the second position to a third position, the bias element 90 may move proximal to the U-shaped portion 98 to release the U-shaped portion 98 from the compressed position and the arm 100 from the catheter adapter 12, and the U-shaped portion 98 may block the distal opening 94 such that the distal tip 28 of the introducer needle 26 is prevented from exiting the distal opening 94 and/or blood is prevent from leaking out of the distal opening 94.

As illustrated in FIGS. 3A-3D, in some embodiments, the bias element 90 may include an inner housing, which may surround the introducer needle 26.

Referring now to FIGS. 4A-4D, in some embodiments, the bias element 90 may include a base 102 and an extension 104 extending distally from the base 102. In some embodiments, the extension 104 may contact the U-shaped portion 98 to bias the spring clip 96 in the compressed position. In some embodiments, the base 102 may include the proximal opening 92 of the bias element 90. In some embodiments, the extension 104 may be spaced apart from the introducer needle 26. In some embodiments, the extension 104 may include a rod or another suitable shape that may not interfere with the introducer needle 26 as it is withdrawn. In some embodiments, the outer housing 88 may include an inner support wall 106. In some embodiments, the extension 104 may extend through the inner support wall 106 and may be slidable through the inner support wall 106.

In some embodiments, when the distal tip 28 is in the first position and the second position, the spring clip 96 may exert a strong force on the extension 104. Thus, in some embodiments, to bias the spring clip 96 and hold the U-shaped portion 98 in the compressed position, the extension 104 may be disposed below the introducer needle 26. In further detail, in some embodiments, the extension 104 may be disposed on a side of the introducer needle 26 opposite a mouth of the U-shaped portion 98 and towards the arm 100. In some embodiments, in response to withdrawal of the distal tip 28 proximally from the second position to a third position, the extension 104 may move proximal to the U-shaped portion 98 to release the U-shaped portion 98 from the compressed position.

Figure 3E:
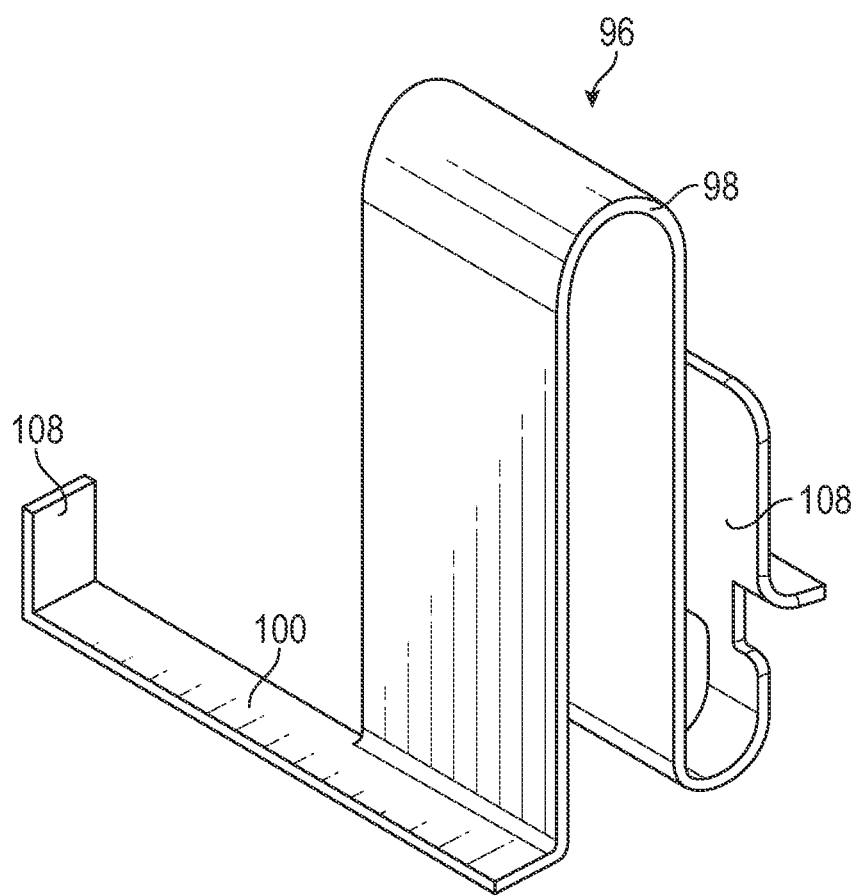
FIG. 3E is an upper perspective view of an example spring clip of the catheter system of FIG. 3A, according to some embodiments.
Figure 4A:
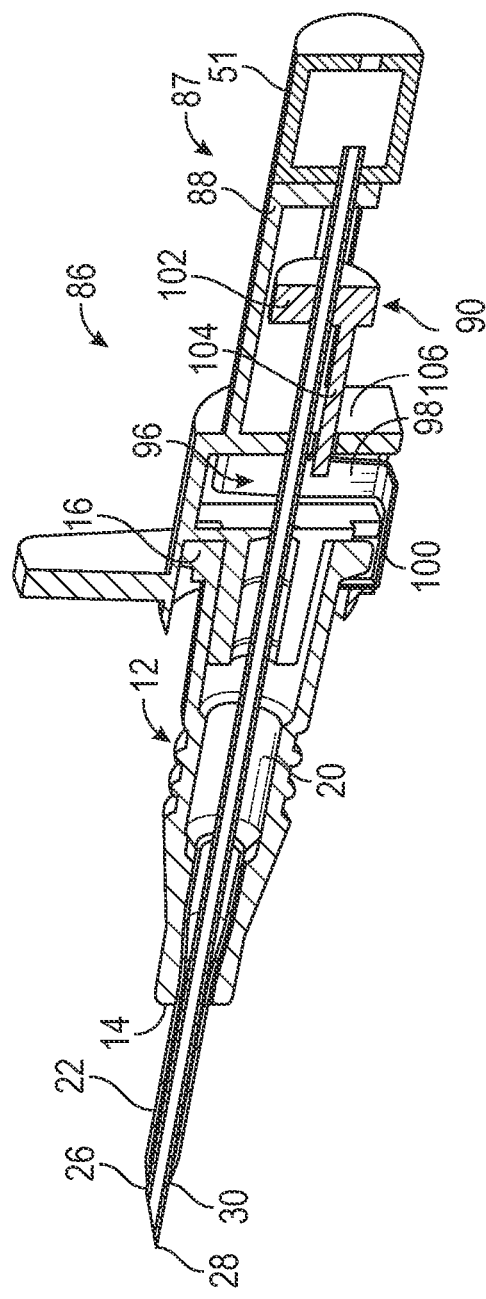
FIG. 4A is cross-sectional view of the catheter system of FIG. 3A, illustrating the distal tip in an example first position and another example bias element, according to some embodiments.
Figure 4B:
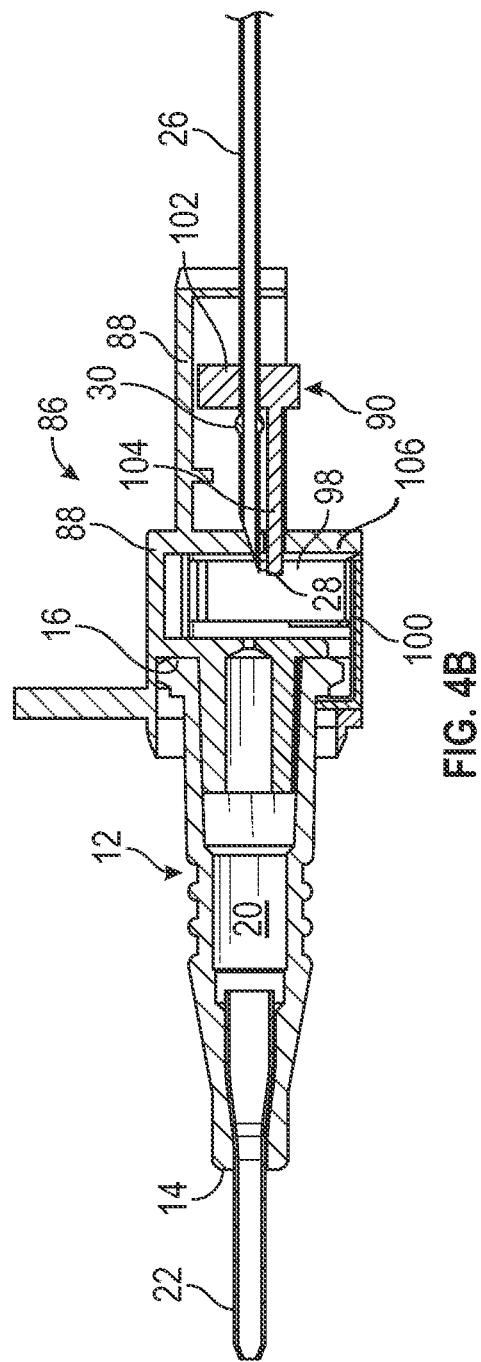
FIG. 4B is a cross-sectional view of a portion of the catheter system of FIG. 3A, illustrating the distal tip in the second position and the other bias element, according to some embodiments.

Referring back to FIG. 3E, the spring clip 96 is illustrated according to some embodiments. In some embodiments, the spring clip 96 include any suitable spring clip. FIG. 3E illustrates the arm 100, the finger 108 angled with respect to the arm 100, the U-shaped portion 98, and a coupler portion 108. In some embodiments, the coupler portion 108 may be coupled to an inner surface of the outer housing 88. In some embodiments, the spring clip 96 may be resilient. In some embodiments, the U-shaped portion may be generally U-shaped, which may include a V-shape or another suitable bend shape. In some embodiments, the spring clip 44 may be constructed of metal or another suitable material.

Referring now to FIG. 4, in some embodiments, one or more of the catheter systems described in the present disclosure may be configured to reduce friction-induced drag force on an introducer needle during withdrawal of the introducer needle from the patient and a catheter assembly. In some embodiments, the reduced friction-induced drag may reduce a likelihood of the clinician accidentally dislodging the catheter from an insertion site and the vasculature. The distance and relative force magnitude values of FIG. 4 are meant to be examples for illustration purposes and are not limiting.

Figure 5A:
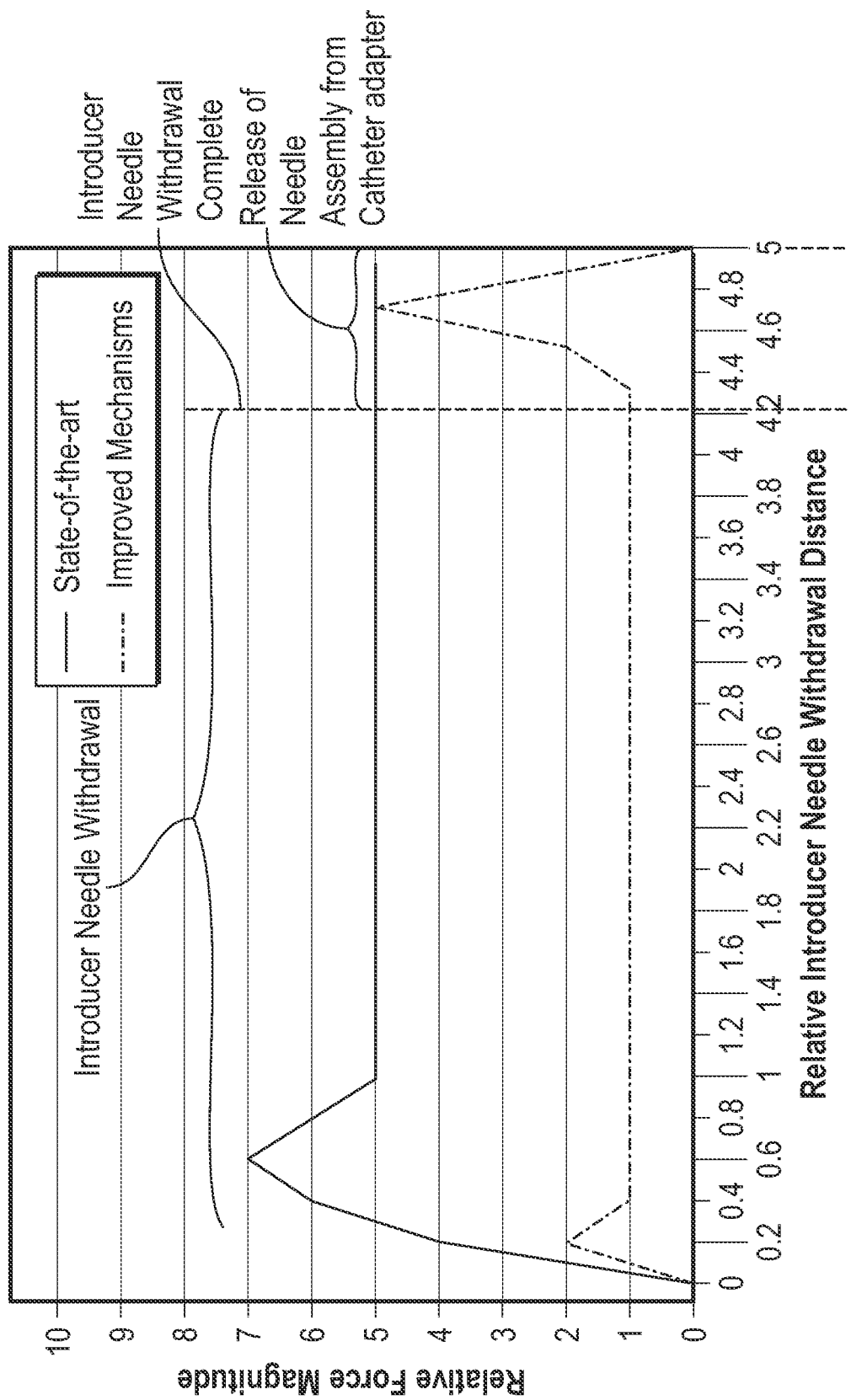
FIG. 5A is a graph illustrating mechanism-induced friction-based drag force versus withdrawal distance, according to some embodiments.

Referring now to FIG. 5A, the catheter system 10, the catheter system 60, and the catheter system 86 may be configured to reduce friction-induced drag force on the introducer needle 26 during withdrawal of the introducer needle 26 from the patient and a catheter assembly, which may include the catheter adapter 12 and the catheter 22. In some embodiments, the graph of FIG. 5A may correspond to one or more of the following: the catheter system 10, the catheter system 60, and the catheter system 86. In some embodiments, the reduced friction-induced drag may reduce a likelihood of the clinician accidentally dislodging the catheter 22 from an insertion site and the vasculature. The distance and relative force magnitude values of FIG. 5A are meant to be examples for illustration purposes and are not limiting.

Figure 5B:
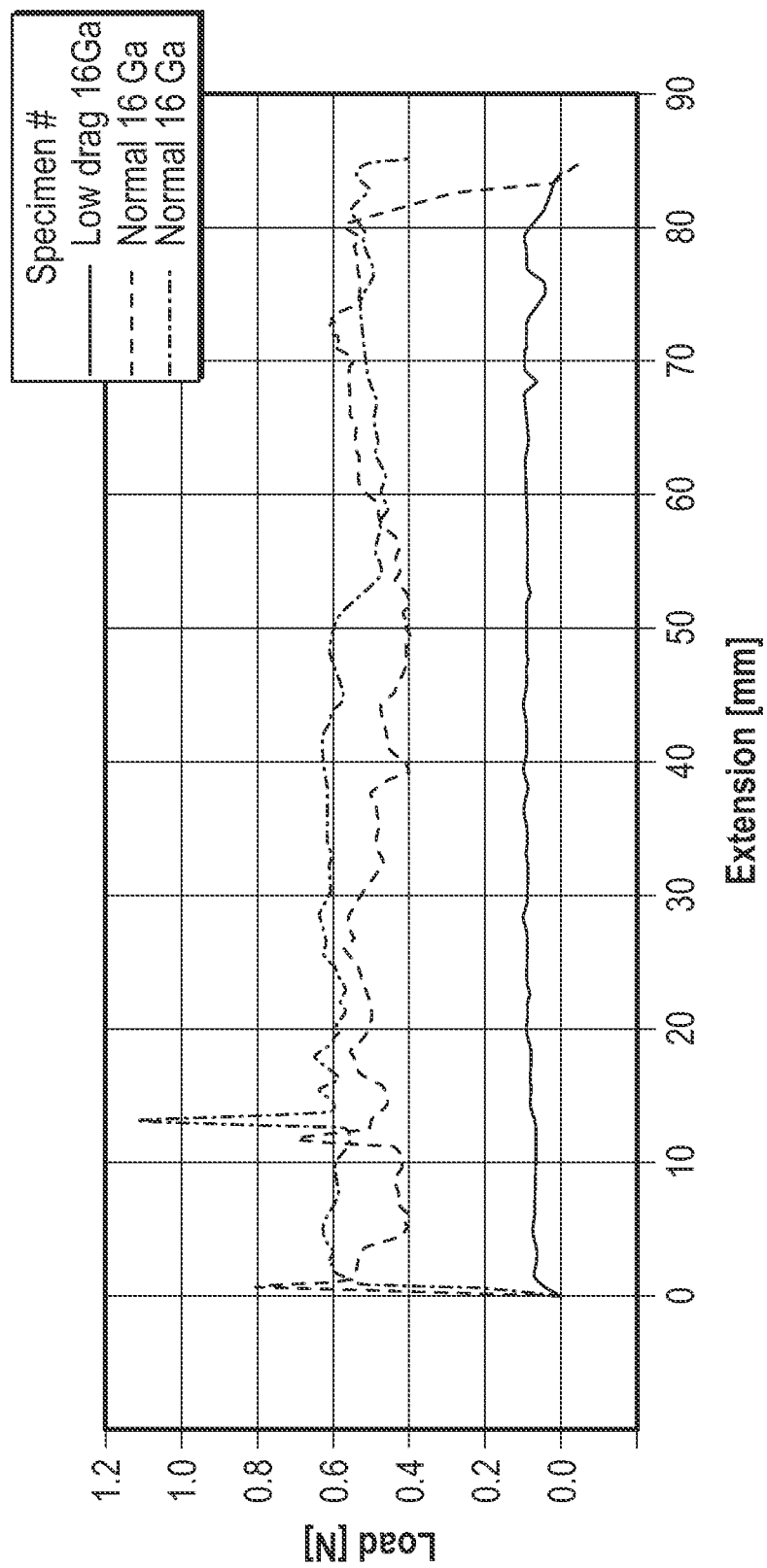
FIG. 5B is a graph illustrating a lower drag force of an example catheter system, according to some embodiments.

FIG. 5B is a graph illustrating a lower drag force of an example catheter system of the present disclosure ("Low drag 16 Ga") versus catheter systems known in the art ("Normal 16 Ga"), according to some embodiments. As illustrated in FIG. 5B, a load on the catheter system ("Low drag 16 Ga") remains lower at various extension or withdrawal distances of the introducer needle compared with the other catheter systems known in the art. The load or drag force for the catheter system ("Low drag 16 Ga") may average at about 0.1 N, while the catheter systems known in the art have a load or drag force of about 0.5 to 0.6N on average. In some embodiments, the catheter system ("Low drag 16 Ga") may include or correspond to the catheter system 86 of FIGS. 3-4 and may be configured to reduce friction-induced drag force on the introducer needle 26 during withdrawal of the introducer needle 26 from the patient.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention. It should be understood that the embodiments may be combined.

We claim:

1. A catheter system, comprising:
   a catheter adapter, comprising a distal end, a proximal end, and a wall forming a lumen, wherein the wall comprises a slot;
   a catheter extending distally from the distal end of the catheter adapter;
   a needle assembly coupled to the catheter adapter, the needle assembly comprising:
      an introducer needle, comprising a distal tip and a bump feature, wherein the distal tip is disposed distal to the catheter in a first position;
      a housing, comprising:
         a distal opening;
         a proximal opening, wherein a diameter of the proximal opening is less than an outer diameter of the bump feature; and
         a side opening, wherein a proximal end of the side opening is distal to a proximal end of the slot; and
      a spring clip disposed within the housing, wherein the spring clip comprises a first end and a second end, wherein the first end comprises a U-shaped portion partially disposed within the slot, wherein the proximal end of the side opening is disposed within the U-shaped portion to bias the U-shaped portion outwardly, wherein the U-shaped portion does not contact the introducer needle, wherein in response to withdrawal of the distal tip proximally from the first position to a second position, the bump feature contacts the proximal opening, wherein in response to withdrawal of the distal tip proximally from the second position to a third position, the housing and the proximal end of the side opening move proximally, the U-shaped portion is released and moves inwardly, and the spring clip blocks the distal opening.

2. The catheter system of claim 1, wherein the first end of the spring clip abuts the proximal end of the side opening.

3. The catheter system of claim 1, wherein the first end of the spring clip comprises a shield portion, wherein the shield portion is generally L-shaped and extends from the U-shaped portion, wherein in response to withdrawal of the distal tip proximally from the second position to a third position, the shield portion blocks the distal opening.

4. The catheter system of claim 3, wherein the first end of the spring clip further comprises a lip extending proximally from the shield portion, wherein the shield portion is disposed in between the lip and the U-shaped portion, wherein in response to withdrawal of the distal tip proximally from the second position to the third position, the distal tip is disposed between the lip and the U-shaped portion.

5. The catheter system of claim 1, wherein the spring clip does not contact the introducer needle.

6. The catheter system of claim 1, wherein the spring clip comprises an opening, wherein the introducer needle extends through the opening, wherein the introducer needle is spaced apart from the opening.

7. The catheter system of claim 1, wherein the spring clip is generally U-shaped between the first end and the second end.

8. The catheter system of claim 1, wherein the housing comprises a groove, wherein the second end of the spring clip is disposed within the groove, wherein in response to withdrawal of the distal tip proximally from the second position to the third position, the housing and the proximal end of the side opening move proximally and the second end moves closer to a distal end of the groove.

\* \* \* \* \*